United States Patent [19]

Regen

[11] Patent Number: 4,485,045

[45] Date of Patent: Nov. 27, 1984

[54] SYNTHETIC PHOSPHATIDYL CHOLINES USEFUL IN FORMING LIPOSOMES

[75] Inventor: Steven L. Regen, Milwaukee, Wis.

[73] Assignee: Research Corporation, Tucson, Ariz.

[21] Appl. No.: 382,296

[22] Filed: May 26, 1982

Related U.S. Application Data

[63] Continuation-in-part of Ser. No. 280,633, Jul. 6, 1981.

[51] Int. Cl.$^3$ .............................. A23J 7/00; C07F 9/10
[52] U.S. Cl. ...................................... 260/403; 264/4.3; 264/4.6; 264/4.7; 424/1.1; 424/19; 424/38; 424/178; 424/199; 427/54.1; 428/402.2; 428/402.22; 428/516; 560/185
[58] Field of Search ........................ 260/403; 424/199

[56] References Cited

U.S. PATENT DOCUMENTS

| Re. 30,748 | 9/1981 | Sears | 260/403 |
| 2,002,885 | 5/1935 | Detwiler et al. | 260/403 X |
| 2,531,275 | 11/1950 | Jones | 260/408 X |
| 2,689,863 | 9/1954 | Broderick et al. | 260/549 X |
| 4,254,115 | 3/1981 | Dawidson et al. | 260/403 X |
| 4,320,121 | 3/1982 | Sears | 260/403 X |

*Primary Examiner*—Richard D. Lovering
*Attorney, Agent, or Firm*—Scully, Scott, Murphy & Presser

[57] ABSTRACT

Lower-ω-alkenoyloxy-long chain alkanoic anhydrides are synthesized from the ω-hydroxyalkanoic acids and are condensed with glycerophosphatidyl cholines to prepare alkenoyloxyalkanoic esters of glycerophosphatidyl cholines. These are used to make vesicles which are then polymerized in situ. These vesicles show improved stability and the rate of leakage of entrapped active ingredients such as drugs can be controlled. They are also used to form a hydrophyllic monolayer on polyethylene.

5 Claims, No Drawings

SYNTHETIC PHOSPHATIDYL CHOLINES USEFUL IN FORMING LIPOSOMES

CROSS-REFERENCE TO RELATED APPLICATION

This application is a continuation-in-part of U.S. patent application Ser. No. 280,633, filed July 6, 1981.

SUMMARY OF THE INVENTION

This invention relates to synthetic phosphatidyl cholines of the structure

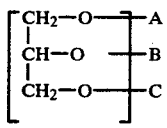

in which

A is

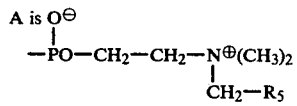

B and C are each $-CO-R_1$ or $-CO-R_2$; in which $-CO-R_1$ is a fatty acid acyl residue of at least six carbons, and $-CO-R_2$ is $-CO-(CH_2)_n-O-CO-CR_3=CHR_4$ in which n is greater than 4, $R_3$ and $R_4$ are each H or $CH_3$; $R_5$ is H or $-CH_2-D$; and at least one of B, C, and D is $-CO-R_2$.

The invention further relates to vesicles having walls comprising the above synthetic phosphatidyl cholines in polymerized form, the said polymers being homopolymers of one such compound, copolymers of two or more such compounds or copolymers of such compounds with up to 20% by weight of a tertiary ammonium salt of the structure

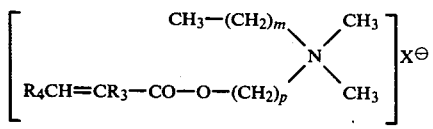

in which $R_3$ and $R_4$ are the same as above and m and p are greater than 7 and $X^\ominus$ is a simple anion. The invention further relates the key intermediate for the synthesis of compounds of Structure I, namely the anhydrides of the structure

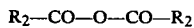

$$R_2-CO-O-CO-R_2$$

in which $R_2$ is as above.

BACKGROUND OF THE INVENTION

Bilayer vesicles or liposomes whose walls comprise phosphatidyl chlorines are being studied as drug carriers, offering the attractive properties of promoting passage of the drugs across cell membranes, increasing drug lifetime in the plasma and retarding drug catabolism. Lipsomes are, however, thermodynamically and biologically unstable and the rate of leakage of entrapped drugs is high. Consequently, their practical utility may be limited.

More recently, the concept of polymerized vesicles, formed from polymerizable material has been proposed (Regen et al., *J. Am. Chem. Soc.* 1980, 102, 6638) as a method of achieving enhanced stability.

THE PRESENT INVENTION

I have found a class of synthetic phosphatide derivatives which can be used to form vesicles and then be polymerized in situ to form much more stable liposomes. By incorporating cross-linking agents in the vesicle formation, a further improvement over the prior art, namely improved control of the permeability of the liposome, is achieved.

The synthetic phosphatidyl cholines of this invention (Structure I) are esters of glycerine in which one hydroxyl carries a phosphatidyl esterifying moiety and at least one of the other hydroxyls carries an unsaturated lower aliphatic acyloxy longer chain alkanoyloxy moiety. Alternatively, the phosphacholine esterifying moiety itself carries an unsaturated lower aliphatic acyloxyethyl quaternizing group in place of one of the quaternary methyl groups in the choline moiety. Any remaining hydroxyl is esterified with a fatty acid moiety of at least six carbons. Those compounds having two unsaturated esterifying moieties can act as the cross-linking agents mentioned about which permit permeability control in the liposomes.

The key intermediates for the compounds of Structure I, themselves a separate part of this invention, comprise the anhydrides of Structure III. A typical such compound is 12-methacryloyloxydodecanoly anhydride of Structure IV:

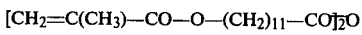

$$[CH_2=C(CH_3)-CO-O-(CH_2)_{11}-CO]_2O \qquad IV$$

Compound IV is prepared by the esterification of 12-hydroxydodecanoic acid with methacryloyl chloride, followed by anhydride formation with ethyl chloroformate and triethylamine. If acryloyl chloride, crotonyl chloride or isocrotonyl chloride are used in place of methacryloyl chloride, there are obtained the variant structures in which $R_3$ or $R_4$ are hydrogen or methyl. The aliphatic chain to which the unsaturated acyloxy group is attached may be any long chain of over six carbons. In such a case the esterification is performed on the appropriate ω-hydroxyalkanoic acid of more than six carbons, such as 16-hydroxypalmitic acid, 18-hydroxystearic acid or 10-hydroxydecanoic acid.

Compounds having an unsaturated lower aliphatic acyloxyethyl quaternizing group are synthesized by condensing the corresponding bromoethoxyphosphoryloxy glyceride with a β-dimethylamino unsaturated lower aliphatic ethyl acrylate such as β-dimethylaminoethyl methacrylate, acrylate or crotonate. When the corresponding bromoethoxyphosphoryloxy glyceride also has a free hydroxyl on the glycerine moiety, it can be further treated as described below.

Compounds of Structure I having two unsaturated chains (i.e., B, C and/or D are $-CO-R_2$) are obtained by esterification of glycerophosphacholine with anhydrides of Structure III. Those having only one unsaturated chain (only one of B or C is $-CO-R_2$) can be obtained by esterifying a lysophosphatidylcholine alkanoyl (such as Lα-lysophosphatidylcholine palmitoyl) with the anhydrides of Structure III. Other lysophosphatidylcholine alkanoyls in which the alkanoyl has more than six carbons such as capryloyl, pelargonoyl, caproyl, undecanoyl, lauroyl, or stearyl can likewise be used.

The vesicles of this invention can be prepared by sonifying the phosphatidyl cholines of Structure I, followed by polymerization in situ by irradiation. Alternatively, the vesicles can be prepared by drowning a solution of the lipid in water. Also alternatively, the polymerization can be initiated by adding a free radical initiator such as azoisobutyronitrile. There may be used a single compound of Structure I or a mixture of such compounds. In addition, up to 20% of the compounds of Structure II can be included as well. The preparation of such compounds is described in the Regen paper mentioned above. Compounds of Structure I in which both B and C are —CO—$R_2$ are cross-linking agents. Control of the rate of leakage of drugs occluded in the vesicles is achieved by varying the proportion of such compounds in mixtures in which B or C is —CO—$R_1$.

Any drugs to be incorporated in the liposomes are included in the solution being sonified. Such drugs may be any orally or intraperitoneally administered systemic drug whose controlled release into the mammalian body is desired, provided it is stable to the sonification and irradiation treatment, if these procedures are used. Alternatively, the other methods of vesicle formation and polymerization are used. Especially important types of drugs to be used in these delivery systems are anti-tumor agents and hormones such as insulin.

It is an advantage of this invention that the liposomes thus prepared from the compounds of this invention are markedly more stable than those prepared with natural lipids. It is a further advantage of this invention that the rate of release of entrapped active ingredients, such as drugs, can be time-controllable by the use of cross-linkage agents.

The compounds of Structure I have further unexpected use which is a further part of this invention. They can be used to modify the surface of solid organic polymers, such as polyethylene, by polymerization on the surface. The polymers of the compounds of Structure I become bonded to the surface—whether by adhesion or by molecular bonding during the polymerization is not known. An approximately monomolecular layer of the polymer on the solid organic polymer is formed.

Surface structure and composition play a significant role in defining many of the physical properties and ultimate uses of polymers. In particular, features such as wetting, weathering, adhesion, dye adsorption, friction, electrostatic charging, permeation, and biocompatibility, which are important for engineering and biotechnological applications, are largely influenced by surface characteristics. Despite this fact, current methods available for modifying polymer surfaces in a well-defined manner remain limited.

The polymer whose surface is to be modified by use of the compounds of Structure I may be any solid hydrophobic organic polymer, preferably a polyolefin such as polyethylene, polypropylene, polybutylene, polystyrene, or the like. The solid is washed with a dispersion of vesicles of the compounds of Structure I and the wetted solid polymer is irradiated to polymerize the coating.

The formation of monolayers on the surface of hydrophobic olefinic polymers is not limited to the compounds of Structure I. More broadly, any amphiphylic lipid having an olefinic polymerizeable substituent can be so used. A large number of such molecules are described, e.g., in the paper of Hub et al., *Angewandte Chemie* (English Edition) 19 (1981) 938, which disclosure is hereby made by reference a part of this specification. These polymerizeable lipids can be used to form vesicles which can then, in turn, be used in the process of this invention to form a monolayer on the surface of an olefinic polymer to give the coated polymers of this invention.

This invention can be illustrated by the following examples.

EXAMPLE 1

To a solution of 2.16 g of 12-hydroxydodecanoic acid in 30 ml of tetrahydrofuran (THF) is added 1.09 g of pyridine. The mixture is cooled to 0° C. and a solution of 1.04 g of methacryloyl chloride in 15 ml of THF is added dropwise. The mixture is allowed to warm to room temperature while stirring an is then stirred at ambient temperature for 12 hours. The solvent is then removed under reduced pressure and the residual solid is dissolved in 25 ml of diethylether. The solution is washed with distilled water, dried over magnesium sulfate and then evaporated to dryness. The product is purified by chromatography, using a 1:2 mixture of ethylacetate and hexane to give 1.5 g (53% yield) of 12-methacryloyloxydodecanoic acid.

To a solution of 0.75 g of 12-methacryloyloxydodecanoic acid in 15 ml of THF is added 0.5 ml of triethylamine. The mixture is cooled to −20° C. and a solution of 0.3 ml of ethylchloroformate in 10 ml of THF is added dropwise. The mixture is then stirred two hours cold, after which it is allowed to warm to ambient temperature, where it is stirred an additional 20 minutes. It is then rechilled to −20° C. and a solution of 0.75 g of 12-methacryloyloxydodecanoic acid and 0.5 ml of triethylamine in 15 ml of THF is added dropwise. The mixture is then stirred overnight at room temperature, after which the solvent is removed under reduced pressure. The crude anhydride is dissolved in 250 ml of ether. The solution is then washed with water, dried over $MgSO_4$ and then evaporated. The residue is dried at 25° C. and 0.1 mm pressure for 24 hours to give 94% yield of the anhydride.

If acryloyl chloride, crotonyl chloride or isocrotonyl chloride is used in equivalent quantities in place of methacryloyl chloride, the corresponding acyloxydodecanoyl anhydride is obtained. Similarly, when other $\omega$-hydroxyalkanoic acid of more than eight carbons are used in this procedure, the corresponding acyloxyalkanoyl anhydride is obtained.

EXAMPLE 2

To a solution of 0.05 g of L-$\alpha$-lysophosphatidyl choline palmitoyl and 0.083 g of the anhydride prepared in Example 1 in 10 ml of chloroform is added 0.018 g of 4-dimethylaminopyridine. the mixture is degassed with nitrogen and then stirred at room temperature in the dark for 72 hours. The reaction is followed by thin layer chromatography (t.l.c.). The stirrer is then removed and the solvent is evaporated under reduced pressure. The residue is picked up in a 4:5:1 mixture of chloroform, methanol, and water. The solution is then passed through a mixture of cationic and anionic resins (AG-501-X8 (D) resin manufactured by Biorad Laboratories). The product is eluted with 20 ml of the same solvent mixture and the eluate is concentrated under reduced pressure. The residue is purified chromatographically on silica gel successively with chloroform and chloroform-methanol mixture. The fractions containing the lecithin-like material, as seen by t.l.c. are collected and evaporated under reduced pressure, to give 0.063 g (83%) of the product of the structure

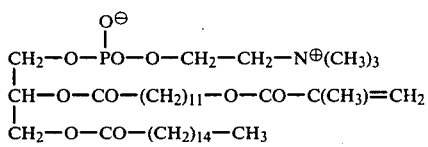

When the corresponding lysophosphatadidyl choline stearoyl or lauroyl is used in place of the palmitoyl compound, the corresponding product is obtained. Similarly the use of the other anhydrides prepared in Example 1 gives the corresponding acyloxy derivative.

EXAMPLE 3

A mixture of 0.488 g of L-α-glycerophosphoryl choline (derived from egg lecithin by hydrolysis) and 3.12 g of the anhydride prepared in Example 1 in 20 ml of chloroform (freshly distilled over $P_2O_5$) is stirred vigorously at room temperature while 0.685 g of 4-dimethylaminopyridine is added. The mixture is then degassed with nitrogen and then stoppered and placed in darkness. It is stirred at room temperature, in the dark, for 72 hours. The solvent is then removed under reduced pressure and the residue is dissolved in 5 ml of a 4:5:1 mixture of chloroform, methanol, and water. The solution is passed through a column of cationic and anionic resins (AG-5010-X8(D)) and the column is washed with 20 ml of the same solvent mixture. The washing is combined with the original solution and the whole is evaporated under reduced pressure. The residual crude product is dissolved in a minimal amount of chloroform and purified by chromatography on silica gel. The elution is successively done with chloroform, 9:1 chloroform-methanol, 1:1 chloroform-methanol and 1:9 chloroform and methanol. The fractions are analyzed by t.l.c. and those containing products with Rf similar to lecithin are combined. Evaporation of the solvent under reduced pressure given 0.534 g (36%) of the product

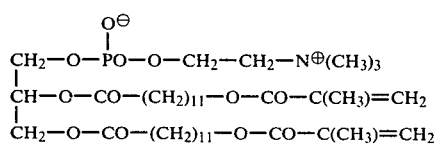

When the other anhydrides of Example 1 are used, the corresponding acyloxydodecanoyl derivatives are obtained.

EXAMPLE 4

To 300 mg of the compound

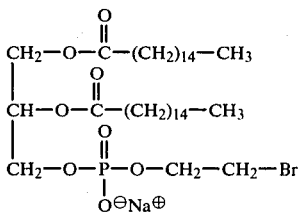

(prepared by the procedure of Eibl, *Chemistry and Physics of Lipids*, 26 (1980) 239–247) is added 4 ml (25.5 mmol) of N,N-dimethylaminoethyl methacrylate. The mixture is stirred at 50° C. for 40 hours. The solution is then cooled to room temperature and 30 ml of acetone is added. After refrigeration at −10° C. for four hours, the white precipitate which forms is collected by filtration, yielding 307 mg of a crude compound of the structure

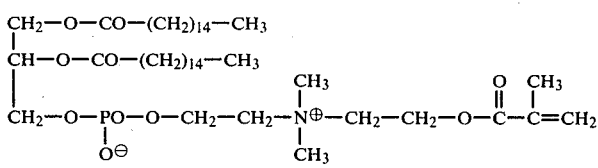

This is purified chromatographically using a 1×16 cm silica gel column and eluting successively with 50 ml of chloroform, 50 ml of 3:1 chloroform-methanol. 100 ml of 1:3 chloroform-methanol and 100 ml of 4:5:1 chloroform-methanol-water. The 192 mg of purified product gives the expected $^1$H nmr and IR spectra and the correct analysis for phosphorus and nitrogen.

EXAMPLE 5

A mixture of 6 mg of the product of Example 2 in 3 ml of $D_2O$ is sonicated for five minutes at 55° C., using a Heat Systems Model W225R bath type sonicator of 155 watts under nitrogen atmosphere. The suspension is then manually shaken for five minutes and then again sonicated for one hour. A Fourier transfer $^1$H nmr spectrum of the resulting clear solution shows the presence of an intact vinyl group. Electron micrographs indicate the formation of closed vesicles of diameters of 350–1400 Å.

EXAMPLE 6

The product of Example 5 is irradiated at 254 nm. Polymerization is complete in one hour. The resultant vesicles are shown by electron micrographs to have retained their spherical shape and approximate size. Attempted extraction with chloroform does not remove monomer or polymer, showing enhance vesicle stability. Removal of water under reduced pressure (0.1 mm, 22 C) followed by IR analysis of the residue shows complete disappearance of monomer.

EXAMPLE 7

The procedure of Example 5 is followed with 2 μCi of ($^{14}$C) sucrose in the water using both the products of Example 2 and Example 3 as starting material. The products are then polymerized by the process of Example 5. The suspension is subjected to gel filtration on Sephadex G-50, using pure water as the eluant. Aliquots (1 ml) of the vesicle suspension are added to presoaked seamless cellulose bags and placed in beakers containing 50 ml of water. At hourly intervals, the bags are changed to new beakers containing 50 ml of water. The results are

| Vesicle | % Retention of ($^{14}$C) sucrose | |
|---|---|---|
| | 4 Hr. | 8 Hr. |
| Unpolymerized, using product of Example 2 | 29 | 16 |
| Polymerized, using product of Example 2 | 65 | 48 |
| Polymerized, using 80% of product of Example 2 and 20% of product of Example 3 | 79 | 69 |

EXAMPLE 8

Commercial low-density polyethylene film, 2-mil (Petrothene NA 344-55; 0.920 g/cm$^3$; 2.0 melt index) was cut into 2×10 cm pieces, then heated for 2 hours in refluxing chloroform-methanol (1:1), then extracted (Soxhlet) with chloroform for 12 hours and finally dried for 6 hours at 78° C. and 0.1 mm pressure. The resulting strips were each placed into 15 ml quartz test tubes, followed by addition of 13 ml of a vesicle dispersion of bis[12-methacryloyloxy)dodecanoyl]-L-α-phosphatidylcholine (the product of Example 2). Each tube was sealed with a No-Air stopper and purged with nitrogen for 10 minutes. It was then placed in a Rayonet photochemical reactor and irradiated for 1 hour (2537-Å). The films were then removed from the tubes, gently hand-shaken in air for ca. 15 s, and washed by immersing them into distilled water (ca. 100 ml) using gentle agitation (each film was moved in and out of the wash six or seven times). The washing procedure was repeated four times using, in each case, freshly distilled water. Finally, the strips were immersed in chloroform-methanol (1:1) for 24 hours at room temperature.

A number of such strips were transferred directly to a pyrex tube and slowly pyrolyzed and analyzed for phosphorus. The average phospholipid content determined from 10 separate preparations was $1.0 \times 10^{-2}$ $\mu$mol. This value corresponds to $1.5 \times 10^{14}$ lipid molecules/cm$^2$ of geometrical surface area. Assuming a cross-sectional area of the product of Example 2 equaling 70 Å$^2$, the maximum packing density of this lipid in a monolayer is $1.4 \times 10^{14}$/cm$^2$. If one also assumes that the geometrical surface and the true surface are identical (i.e., that the film is perfectly flat), the presence of a monolayer is clearly indicated. Direct examination of the phosphatidylcholine-modified film by electron microscopy showed that the surface appeared flat and featureless. Interestingly, the film was sufficiently and uniformly conducting that direct imaging was possible; untreated polyethylene could not be observed because of excessive charging.

In an effort to obtain molecular specific information at the film surface, the attenuated total reflectance IR (ATR IR) spectrum was taken. Only a weak but distinct carbonyl absorption band at 1732 cm$^{-1}$ was clearly visible. Spectra of pure polyethylene or the germanium reflection element alone showed no observable carbonyl band. Further, the phospholipid modified polyethylene was observed to be hydrophyllic and readily wettable.

Stability experiments indicate that the phospholipid membrane remains securely fastened to the polyethylene support even after exposure to THF, methanol, chloroform-methanol (1:1), or 1% aqueous sodium dodecylsulfate for 24 hours at room temperature. Control experiments performed with polyethylene and the product of Example 2 in the absence of uv light, and with polyethylene plus dipalmitoyl-L-α-phosphatidylcholine (with uv irradiation) shows negligible phospholipid incorporation and retention of the hydrophobic surface.

I claim:

1. A compound of the structure

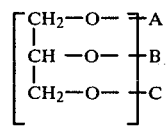

in which A is

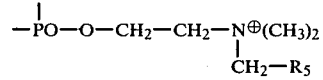

B and C are each —CO—R$_1$ or —CO—R$_2$; in which —CO—R$_1$ is a fatty acid acyl group of at least 6 carbons, and —CO—R$_2$ is —CO—(CH$_2$)$_n$—O—CO—CR$_3$=CHR$_4$ in which n is greater than 4, and R$_3$ and R$_4$ are each hydrogen or methyl; R$_5$ is hydrogen or —CH$_2$—D, wherein D is —CO—R$_2$ and at least one of B, C, and D is present in the compound as —CO—R$_2$.

2. A compound of claim 1 in which B is —CO—R$_1$ and C is —CO—R$_2$.

3. A compound of claim 2 in which —CO—R$_1$ is —CO—(CH$_2$)$_{15}$—CH$_3$ and —CO—R$_2$ is —CO—(CH$_2$)$_{11}$—O—CO—C(CH$_3$)=CH$_2$.

4. A compound of claim 1 in which B and C are both —CO—R$_2$.

5. A compound of claim 4 in which —CO—R$_2$ is —CO—(CH$_2$)$_{11}$—O—CO—C(CH$_3$)=CH$_2$.

* * * * *